United States Patent [19]

Caporiccio et al.

[11] Patent Number: 4,591,444
[45] Date of Patent: May 27, 1986

[54] PROCESS FOR EXHAUSTIVELY DECONTAMINATING PERFLUOROPOLYETHEREAL OILS

[75] Inventors: Gerardo Caporiccio, Milan; Ezio Strepparola, Treviglio, both of Italy

[73] Assignee: Montedison S.p.A., Milan, Italy

[21] Appl. No.: 711,361

[22] Filed: Mar. 13, 1985

[30] Foreign Application Priority Data

Mar. 15, 1984 [IT] Italy .................... 20061 A/84

[51] Int. Cl.$^4$ ............ C02F 1/32; C02F 1/76
[52] U.S. Cl. .................... 210/748; 210/750; 210/753; 210/754; 210/758; 210/908; 568/677
[58] Field of Search ......... 210/748, 749, 750, 753, 210/754, 758, 908, 909, 766; 568/677; 204/149

[56] References Cited

U.S. PATENT DOCUMENTS

| | | | |
|---|---|---|---|
| 3,901,806 | 8/1975 | Murchison | 210/748 |
| 4,012,321 | 3/1977 | Koubek | 210/748 |
| 4,118,398 | 10/1978 | Martini | 568/677 |
| 4,201,876 | 5/1980 | Griffin | 568/677 |
| 4,402,836 | 9/1983 | Fochtman et al. | 210/748 |

FOREIGN PATENT DOCUMENTS 2833337 2/1980 Fed. Rep. of Germany ...... 210/748

*Primary Examiner*—Benoît Castel

[57] ABSTRACT

A process for fully removing from the perfluoropolyethers having a minimum vapor tension, the organic polluting matters containing group —OH and/or bonds

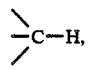

consisting in treating the perfluoropolyether with oxygen, or chlorine or fluorine, at a high temperature and in the presence of ultraviolet radiations, in order to convert the impurities to volatile degradation products easily removable by degassing.

3 Claims, No Drawings

PROCESS FOR EXHAUSTIVELY DECONTAMINATING PERFLUOROPOLYETHEREAL OILS

THE PRIOR ART

There are known perfluoropolyethers having the structure represented by the following general formula:

$$R_f-(CF_2CFXO)_m(CF_2)_n-R'_f \qquad (I)$$

wherein: $X=F$, $CF_3$; $R_f$ and $R'_f$, like or unlike each other, consist of $CF_3$, $C_2F_5$, $C_3F_7$ and n is 0 or an integer and m is an integer such that m/n may range from 0.5 to 30, while the sum (m+n) ranges from 3 to 200; furthermore, when n=o and $X=CF_3$, then $R_f$ and $R'_f$ are preferably $C_2F_5$ and $C_3F_7$.

These products are endowed with high chemical, physical and thermal stabilities and exhibit marked lubricating properties thanks to which they are employable as operative fluids at a minimum vapour tension, for vacuum pumps of the mechanical or diffusion type, and in the mechanical and electronic field.

Due to their chemical inertia they are suitable for being utilized in particular in the vacuum field when it is necessary to remove or to pump aggressive gases such as, for example, halogen, haloid acids, the anhydrides of the Lewis acids or the Lewis acids themselves.

As a consequence of such use, the perfluoroethereal oils of structure (I), which are very resistant by themselves, may progressively get charged with increasing amounts of insoluble and polluting products in suspension. When, after a utilization period, it is necessary, for maintenance or repair operations, to clean the apparatus, the perfluoropolyethereal lubricant needs to be recovered (f.i. by filtration) and purified.

The processes generally known for the purification of the perfluoropolyethereal oils from hydrogenated organic substances, from water, from the suspended metallic or inorganic solid residues, are based on physical separations such as filtration, centrifugation, extraction with solvents, distillation. Drying can be operated by suitable dehydrating agents, which are brought into contact, for a prolonged period of time, with the perfluoropolyethereal oil, or by evaporation under vacuum or in a nitrogen stream in hot conditions.

The processes described hereinabove do not prove to be effective enough to satisfactorily remove the last traces of organic substances contained in the perfluoropolyethereal oils. By consequence they do not exhibit, after such treatments, the same properties of chemical resistance, stability to heat and to oxidation they originally possessed, due to such even very low contents of hydrogenated substances.

THE PRESENT INVENTION

The applicant has now found a process by which it is possible to remove from perfluoropolyethers having a minimum vapour tension, also traces of impurities consisting of organic compounds containing other bonds than those C—O, C—F, C—C, reducing such impurities to levels comparable with the ones which are typical of the perfluoropolyethers obtained from the above cited synthesis processes, i.e. to such contents as to be at the sensitivity limits of the analytical methods, for example to contents of groups

below 2-3 ppm and to contents of groups —OH below 1-2 ppm, by subjecting the perfluoropolyethereal oils containing the said organic impurities to a reaction with oxygen, or chlorine or fluorine, as agents capable of forming radicals which interact with bonds

and also with the —OH groups, or of inducing the formation of radicals in said hydrogenated organic impurities.

Such treatment is accomplished by feeding perfluoropolyether preheated to a temperature from 150° to 200° C., in the liquid state, into a reaction chamber where it comes into contact with one of the gaseous reagents indicated hereinabove. To obtain a more effective action of such reagents, the reaction chamber is irradiated with ultraviolet rays coming from a Hg vapor lamp and having a wave-length preferably from 240 to 600 nm.

The reaction with the organic impurities containing

bonds and/or —OH groups causes the formation of volatile degradation products such as $CO_2$, HF, HCl, carbon halides, which are successively removed from the perfluoropolyethereal oil by degassing under vacuum. Perfluoropolyether is inert under the said reaction conditions. After treatment, the product purity is checked by analyses of the type:

Fourier Transform (FT)-NMR
Fourier Transformer (FT)-I.R.

or by means of the oxygen impact strength test, with oxygen being conveyed under a pressure of 140-180 atm. at a starting temperature of 60° C. according to the test already described.

The process according to the invention is particularly useful when it is carried out downstream of usual physical purification processes, such as filtration, centrifugation, extraction with solvents, which are already known to those skilled in the art, in order to remove the considerable amounts of hydrogenated and/or solid impurities from the perfluoropolyethereal oil. In fact, by means of such physical processes it is not possible to exhaustively remove the last traces of polluting compounds, which, conversely, are removed by the process according to this invention.

The following examples are given to illustrate the possible embodiments of the invention, without being however a limitation thereof.

EXAMPLE 1

The process was conducted in a glass reactor having a capacity of 1.5 l, a length of 30 cm and an inside diameter of 8 cm, equipped with a heating band thermoregulated at 150° C. and, on the head, with a quartz sheath having an outside diameter of 6 cm, in which an ultraviolet-ray lamp, type Hanan TQ81, 150 W power was immersed, with a pipe for the inflow of the perfluoropolyethereal oil, the end of such pipe being equipped with an orifice of 1 mm diameter, with a dipping pipe on the reactor bottom for feeding a reagent in the gas phase, with a vertical raiser having a 2-cm diameter and a 20-cm length, connected to the upper end of a trap cooled by means of $CO_2$ and connected to a vacuum pump capable of maintaining a pressure of 200 Torr. Into the reactor, equipped with a discharge on the bottom connected with a surge tank maintained at 1 Torr, there were introduced, through the capillary orifice, at first 100 g of perfluoropolyethereal oil preheated at 175° C., then gaseous fluorine at the rate of 10 Nml/min. The perfluoropolyether of structure (I) with $X=CF_3$, had a viscosity of 250 c.St. at 20° C. and revealed, on FT-I.R. analysis, a content of

of about 100 ppm and of —Oh of about 50 ppm. The perfluoropolyethereal oil was further fed at a rate of 200 g/hour, while an equal amount thereof was discharged from the bottom discharge pipe. The discharged liquid was made to flow into the surge tank maintained at 1 Torr, in which degassing of the product was completed. The perfluoropolyether so obtained, subjected to FT-IR analysis, revealed to contain not more than 2 ppm of

groups and less than 1 ppm of —OH groups.

EXAMPLE 2

The reactor of example 1 was utilized and it was operated continuously, charging at first 1000 g of perfluoropolyethereal oil preheated at 175° C. Gaseous chlorine was introduced at a rate of 20 N.ml/min. and it was irradiated with ultraviolet light. The treated perfluoropolyethereal oil had structure (I) where $X=CF_3$, exhibited a viscosity of 250 c.St. at 20° C. and on FT-IR analysis revealed to contain about 100 ppm of groups

and 50 ppm of groups —OH. 200 g/hour of oil to be treated were continuously fed and an equal amount of treated product was discharged, which was conveyed into the surge tank under 1 Torr vacuum. The product, analyzed at the surge tank outlet, resulted to contain about 2 ppm of groups

and an equal amount of —OH groups.

EXAMPLE 3

The same reactor of example 1 was utilized and the same operative modalities with the same ultraviolet lamp were followed. 200 g/hour of a perfluoropolyethereal oil of structure (I), wherein $X=F$, having a viscosity of 250 c.St. at 20° C. and containing, as revealed by FT-IR analysis, about 150 ppm of groups

and 80 ppm of groups —OH, were continuously introduced. 20 N.ml/min. of oxygen were introduced into the reactor, maintained at a pressure of 200 Torr and at a temperature of 175° C. After treatment with oxygen, the perfluoropolyethereal oil was sent to the surge tank under a 1 Torr vacuum for the degassing and then it was discharged.

The product so treated revealed to contain, on FT-IR analysis, 1 ppm of groups —OH and, on FT-NMR analysis, 2 ppm of groups

What we claim is:

1. A process for completely removing from a perfluoropolyether having a minimum vapor tension, organic polluting substances containing group —OH and/or

bonds, which consists of treating the perfluoropolyether in the liquid state, at a temperature ranging from 150° to 200° C., with a gaseous reagent selected from oxygen, chlorine, fluorine, and in the presence of ultraviolet radiations of a wavelength ranging from 240 to 600 nm, thereby converting the polluting substances into volatile degradation products, and removing the volatile degradation products by degassing the perfluoropolyether.

2. The process according to claim 1, wherein the degassed perfluoropolyether contains less than 3 ppm of groups

and less than 2 ppm of residual —OH groups.

3. The process according to claim 1, in which the degassing of the treated perfluoropolyether is accomplished under vacuum.

* * * * *